United States Patent [19]

Haas et al.

[11] Patent Number: 4,492,866
[45] Date of Patent: Jan. 8, 1985

[54] METHOD FOR PREDICTING THE PERFORMANCE OF CATHODE MATERIALS

[75] Inventors: George A. Haas, Alexandria, Va.; Arnold Shih, Potomac, Md.; Christie R. K. Marrian, Alexandria, Va.

[73] Assignee: The United States of America as represented by the Secretary of the Navy, Washington, D.C.

[21] Appl. No.: 490,994

[22] Filed: May 2, 1983

[51] Int. Cl.$^3$ .................... H01J 40/00; H01J 47/00
[52] U.S. Cl. .................... 250/305; 250/307
[58] Field of Search ............... 250/305, 306, 307, 310

[56] References Cited

U.S. PATENT DOCUMENTS

| | | | |
|---|---|---|---|
| 3,337,729 | 8/1967 | Thomas et al. | 250/307 |
| 3,631,238 | 12/1971 | MacDonald | 250/305 |
| 3,965,351 | 6/1976 | Strongin et al. | 250/305 |
| 4,034,220 | 7/1977 | le Gressus et al. | 250/310 |
| 4,134,014 | 1/1979 | Neave et al. | 250/310 |
| 4,142,145 | 2/1979 | Haas et al. | 250/307 |

OTHER PUBLICATIONS

Harris, "Analysis of Materials by Electron-excited Auger Electrons", J. of Applied Phys., vol. 39, No. 3, (Feb. 15, 1968).

Primary Examiner—Bruce C. Anderson
Attorney, Agent, or Firm—Robert F. Beers; William T. Ellis; Vincent T. Pace

[57] ABSTRACT

A method for predicting the proclivity of various materials to emit electrons, and thus their suitability for cathode fabrication. The method includes steps to determine the surface work function lowering by analyzing and comparing the Auger electron-energy spectra of a plurality of sample materials.

11 Claims, 2 Drawing Figures

METHOD FOR PREDICTING THE PERFORMANCE OF CATHODE MATERIALS

BACKGROUND OF THE INVENTION

The subject invention relates generally to the measurement of surface properties of electron-emissive materials and, more particularly, to a method for predicting the suitability of various materials for use in electron-emissive cathodes.

Modern dispenser cathodes which are used in most microwave tube applications are usually composed of a metal matrix which has been impregnated with an alkaline earth metal compound. This compound, when heated, dispenses material onto the surface of the matrix metal which then forms a layer on the surface which makes the surface a good electron emitter. This is accomplished due to a lowering of the electronic surface barrier, that is, the surface work function.

The material which forms the layer on the surface is an oxide of the alkaline earth metal (e.g., Barium oxide). A crucial factor in the surface work function lowering is the dipole moment of the molecules of the surface layer material. This dipole is known to be different for different combinations of materials. It would therefore be desirable to have a means for predicting the dipole of various combinations of cathode materials without having to fabricate actual cathodes from those materials and then measure the thermionic emission properties of each one.

The charge transfer that takes place between the alkaline earth metal and the oxygen atoms gives an indication of the magnitude of the dipole moment when the surface layer material is adsorbed on a particular cathode substrate. The inventors have discovered that the extent of this charge transfer can be determined by analysis of the Auger electron energy spectrum of the cathode material.

Electron spectroscopy, and in particular Auger electron spectroscopy, are well-known methods for analyzing surface properties of materials. For example, in "Analysis of Materials by Electron-Excited Auger Electrons", L. A. Harris, J. of Appl. Phys., Vol. 39, No. 3, 1419 (Feb. 15, 1968), it is disclosed that the compositions of surface materials may be analyzed by observing the energy spectrum of Auger electrons emitted by a sample which has been bombarded with an electron beam. The energy spectrum observed is characteristic of the composition and may be used to identify its component elements.

U.S. Pat. No. 3,361,238, MacDonald, discloses a method based on Auger electron spectroscopy, for measuring the electric potential on the surface of a material. MacDonald obtains direct quantitative measurement of the electronic potential by measuring the shift in energy levels of the Auger peaks between two consecutively analyzed points on the material surface.

U.S. Pat. No. 3,965,351, Strongin et al., discloses a method of Auger spectroscopy of dilute alloy surfaces. According to Strongin et al., the electron beam scan is alternated between a pure reference sample and a sample of the material under test. The electrical signal produced at the reference sample is processed such that it is subtracted from the signal produced at the test material sample. The difference signal then represents an Auger spectrum of the trace impurity.

Although all of the above references utilize Auger spectrum analysis, none of them either concerns or discloses methods for measuring surface dipole strength or work function lowering. These references are primarily directed to identification of materials. However, there have been some efforts to measure surface work function parameters.

U.S. Pat. No. 3,337,729, Thomas et al., discloses a method and apparatus for investigating the variation in surface work function of a material. The method is directed to scanning the surface of a sample of the material with an electron beam. The electrical signal produced by the scanning electron beam at the target material is then processed and visually displayed. The shadings in the visual display are representative of the variations in the surface work function across the material surface.

U.S. Pat. No. 4,142,145, Haas et al., discloses a method for measuring surface work function which utilizes low-energy electron reflections to determine the electron affinity and to locate the conduction-band edge relative to the Fermi level at the surface of single-crystal semiconductor material. A beam of electrons is directed onto the material surface. The current collected by the semiconductor is then analyzed as a function of beam energy in order to determine both the position of the conduction band edge with respect to the Fermi level and the electron affinity. The surface work function can then be determined from these two quantities.

Although both of the above cited references disclose methods for measuring surface work function parameters, neither discloses a method for predicting surface work function lowering by measuring charge transfer from interatomic Auger transitions.

In light of the foregoing discussion it appears that there is presently no known method for estimating surface work function lowering due to the formation of a dipole moment, much less one utilizing Auger spectrum analysis.

OBJECTS OF THE INVENTION

Accordingly, one object of this invention is to predict the suitability of various combinations of materials for use in fabricating cathodes.

Another object of this invention is to obtain a measure of the surface work function lowering in various cathode materials.

A further object of this invention is to measure surface work function lowering in cathode materials by means of Auger electron energy spectrum analysis.

SUMMARY OF THE INVENTION

The above and other objects are realized in the present invention which comprises a method for analyzing a plurality of sample cathode materials in order to determine which materials will have the optimum electron emissive characteristics. The cathode material samples consist of metal or metal alloy substrates which have been surface coated with an alkaline earth. The samples are subjected to standard Auger spectrometry which includes impinging an electron beam on the samples and recording the Auger electron-energy spectra.

These Auger spectra are then analyzed by evaluating the relative magnitudes of two adjacent peaks. The peaks to be analyzed correspond to the core-core valence Auger transitions. The relative degree of charge transfer between the alkaline earth metal and the oxygen atoms is then determined by comparing the variations in the relative magnitudes of the aforesaid peaks in the spectra from the various samples. The samples which have the largest degree of charge transfer (i.e., dipole moment) may then be predicted to be the most suitable for use in fabricating cathodes, since they will have the largest degree of surface work function lowering.

Other objects, advantages, and novel features of the invention will become apparent from the detailed description of the invention which follows the accompanying drawings wherein:

DETAILED DESCRIPTION OF THE INVENTION

The method of the present invention is practiced by first preparing the samples to be screened. In the preferred embodiment this is accomplished by depositing on a ribbon, metal alloys of varying composition. For instance, in the experiments carried out by the inventors the ribbon was composed of tungsten-iridium (W-Ir) alloys which varied from 90% W, 10% Ir on one end, to 10% W, 90% Ir on the other.

It should be noted, however, that a continuously varying sample is not necessary to practice this method. Discrete samples may be used. The continuously varying samples, however, allow for greater rapidity in making measurements.

After the metal alloy samples have been prepared, their surface is coated with an alkaline earth. In the experiment conducted by the inventors this step was accomplished by vacuum evaporation deposition to form a surface layer of BaO. Other deposition methods could be used, however (e.g., diffusion of impregnants from the body of the substrate matrix, or co-sputter deposition).

Figure 1:
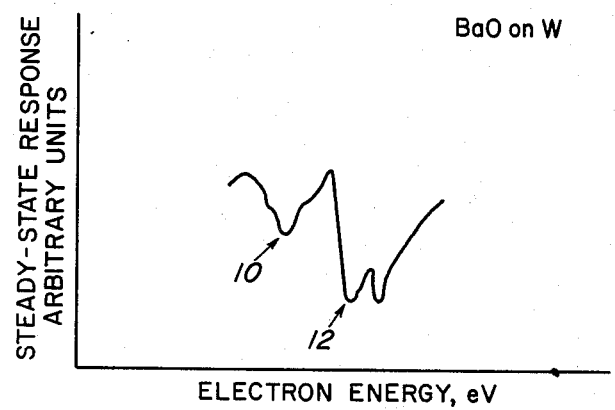
FIG. 1 shows a portion of the Auger spectrum for a thin layer of Barium Oxide (BaO) on a tungsten (W) substrate.
Figure 2:
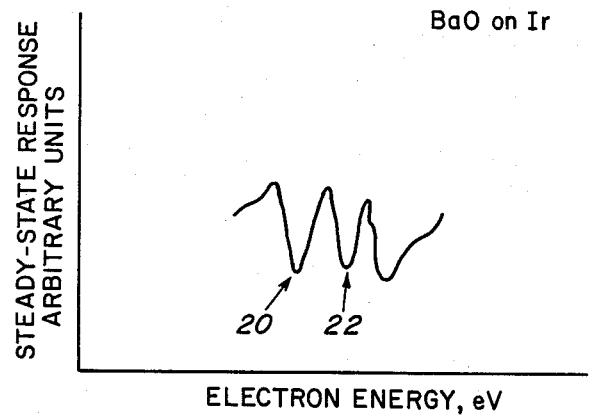
FIG. 2 shows a portion of the Auger spectrum for a thin layer of BaO on an Iridium (Ir) substrate.

Once the sample surface has been coated it can be surveyed point by point (or in the case of discrete samples, sample by sample). This survey is done with standard Auger instrumentation and the Auger electron energy spectrum at each point on the ribbon sample is obtained and recorded. FIGS. 1 and 2 are representations of such Auger spectra for the cases of BaO on W and BaO on Ir, respectively.

The relative degree of charge transfer between the Ba and O atoms is determined by analysis of the relative heights of two adjacent interatomic peaks in the Auger spectra of the various samples. For the case of BaO the two interatomic Auger peaks considered are the 68 volt and 73 volt peaks.

These two peaks are the result of Auger transitions involving the Ba 4d and 5p core states. The 68 v peak results from an oxygen 2p valence state and the 73 v peak is from a barium 6s valence state. The 68 volt peak represents Ba atoms which have given their electrons to the O atom. The 73 volt peak represents Ba atoms which have not done so. Thus the difference in magnitude of these two peaks gives an indication of the amount of charge transfer that has taken place between Ba and O atoms.

FIG. 1 shows the Auger spectrum for BaO on W, showing a 68 volt peak (10) and a 73 volt peak (12). FIG. 2 is the Auger spectrum for BaO on Ir, showing a 68 volt peak (20) and a 73 volt peak (22). It can be seen that the 68 volt peak (20) for the case of BaO on Ir is much larger, compared to the 73 volt peak (22), than the 68 volt peak (10) is, compared to the 73 volt peak (12) for the case of BaO on W. This indicates that a much larger charge transfer exists for the BaO on Ir case, and that the BaO dipole moment on an Ir substrate is significantly larger than on a W substrate. Thus it can be determined from these results that the work function lowering for BaO on Ir would be larger than for BaO on W. In fact, this conclusion has been confirmed by actual thermionic emission measurements. The work function lowering was $\approx 3.5$ volts for the Ir substrate, while for the W substrate it was $\approx 2.5$ volts.

The immediately preceding discussion would, of course, be limited to the case where there are only two discrete samples: one having a 100% W substrate, the other having a 100% Ir substrate. Generally, in practicing the method of this invention there will be numerous samples with various concentrations of a given alloy system. Therefore, the number of spectra to be analyzed and compared would be much greater. The same Auger measurements, however, can be used to identify the various substrate concentrations so that each combination can be compared with every other one. In this manner, the combination with the optimum work function lowering can be determined from amongst the various alloys.

Although BaO was utilized as the surface layer material in the actual experiments done, other alkaline earths or combinations thereof may be used. Likewise, although W and Ir were utilized as the substrate metals, virtually any metal or metal alloy could be used.

Obviously, numerous modifications and variations of the subject invention are possible in light of the above teachings. It is, therefore, to be understood that within the scope of the appended claims, the invention may be practiced otherwise than as specifically described herein.

What is claimed as new and desired to be secured by Letters Patent of the United States is:

1. A method for predicting the suitability of various materials for use in fabricating cathodes comprising the steps of:
   (a) preparing a plurality of samples having various concentrations of metal substrate materials,
   (b) forming a surface layer on said samples with an alkaline earth compound,
   (c) measuring the relative magnitudes of at least two adjacent interatomic Auger peaks for each sample,
   (d) determining from said relative magnitudes the relative degree of charge transfer between the alkaline earth metal and oxygen atoms for each sample, and
   (e) comparing the relative degree of charge transfer of each sample with every other sample, whereby the suitability of the various materials for use in fabricating cathodes may be predicted.

2. The method as recited in claim 1 wherein the step of measuring the relative magnitudes of the two Auger peaks for each sample further comprises the steps of:
   (a) impinging an electron beam upon the surface of each of said samples,
   (b) recording the Auger electron energy spectrum of secondary electrons emitted by the surface of each of said samples over a range of energy levels including at least two adjacent interatomic Auger peaks, and (c) evaluating the relative magnitudes of said Auger peaks.

3. The method of claim 2 wherein the step of recording the Auger energy spectra further comprises the step of identifying in said spectra the two Auger peaks which result only from core-core valence Auger transitions, where one of said peaks results from an oxygen valence state and the other results from a valence state of the alkaline-earth metal.

4. The method of claim 3 wherein the step of preparing a plurality of samples having various concentrations of metal substrate materials further comprises the step of preparing a strip of sample material by depositing alloys of at least two different metals on a substrate, such that the ratio of the concentrations of said metals varies continuously from one end of said strip to the other.

5. The method of claim 4 wherein the step of preparing the strip of sample material further comprises the step of varying continuously the ratio of the concentrations of the metals from approximately 9:1 at one end of the strip of sample material to approximately 1:9 at the other end.

6. The method of claim 5 wherein the step of preparing the strip of sample material further comprises depositing alloys which include Tungsten and Iridium on the substrate.

7. The method of claim 6 wherein the step of forming a surface layer of the samples is accomplished by vacuum deposition and annealing of the alkaline earth metal compound on the surface of the sample material.

8. The method of claim 7 wherein the step of forming a surface layer on the samples is accomplished by evaporation and annealing of the alkaline earth metal compound on the surface of the sample material.

9. The method of claim 8 wherein the step of forming a surface layer on the strip of sample material further comprises evaporating and annealing Barium on the surface of the sample material.

10. A method for predicting the suitability of various materials for use in fabricating electronic cathodes comprising the steps of:
(a) preparing a plurality of samples of alloys including Tungsten and Iridium having various concentrations of each,
(b) forming a surface layer on said samples with Barium oxide,
(c) impinging an electron beam upon the surface of each of said samples,
(d) recording the Auger electron energy spectrum of secondary electrons emitted by the surfaces of said samples over a range of energy levels including at least the two Auger peaks corresponding to the interatomic Barium-Oxygen Auger transitions;
(e) evaluating the relative magnitudes of said Auger peaks,
(f) determining from said relative magnitudes the relative degree of charge transfer between the barium and oxygen atoms for each sample, and
(g) comparing the relative degree of charge transfer of each sample with every other sample, whereby the suitability of the various materials for use in cathode fabrication may be predicted.

11. The method of claim 10 wherein the step of recording the Auger energy spectra of the samples over a range of energy levels further comprises the step of recording said Auger energy spectra over a range of energy levels including the 68 volt and 73 volt Barium Auger peaks.

* * * * *